United States Patent [19]
Zirm

[11] Patent Number: 5,628,793
[45] Date of Patent: May 13, 1997

[54] ARTIFICIAL LENS

[76] Inventor: Mathias Zirm, Fallmerayerstrasse 13, A-6020, Innsbruck, Austria

[21] Appl. No.: 241,221

[22] Filed: May 10, 1994

[30] Foreign Application Priority Data

Mar. 18, 1994 [DE] Germany .................. 44 09 217.2

[51] Int. Cl.$^6$ .................. A61F 2/14; A61F 2/16
[52] U.S. Cl. .................. 623/4; 623/5; 351/160 R
[58] Field of Search .................. 623/4–6; 351/160 R

[56] References Cited

U.S. PATENT DOCUMENTS

| | | | |
|---|---|---|---|
| 4,158,030 | 6/1979 | Stoyan | 623/4 |
| 4,240,163 | 12/1980 | Galin | 623/6 |
| 4,253,199 | 3/1981 | Banko | 623/6 |
| 4,264,493 | 4/1981 | Battista | 623/4 |
| 4,908,404 | 3/1990 | Benedict et al. | 525/54.11 |
| 5,201,762 | 4/1993 | Hauber | 623/6 |
| 5,340,583 | 8/1994 | Dziabo et al. | 424/412 |

*Primary Examiner*—Mary Beth Jones
*Attorney, Agent, or Firm*—Robbins, Berliner & Carson, LLP

[57] ABSTRACT

An artificial lens which specifically simulates the human eye in its mechanical properties. It is possible to produce the lens directly from a peptide mixture. The lens can be either homogeneous or multilayered in structure.

22 Claims, 1 Drawing Sheet

ARTIFICIAL LENS

BACKGROUND OF THE INVENTION

The invention concerns an artificial lens for simulation of the human lens in the eye. Until now, in so-called "star operations [cataract removal]", the human lens has been removed and replaced with an artificial lens.

In this process, it is known to remove the existing human lens (i.e., the lens nucleus) in its entirety from the capsular sac. The lens consists of a lens nucleus, a lens cortex, and a lens capsule, which surrounds the lens.

The lens capsule must be removed at the beginning of the operation (preferably by means of capsular hexis).

At the end of such an operation, an artificial lens is inserted for reasons of optical rehabilitation.

Techniques are currently known for simulating such an operation on practice eyes. Here, as a rule, animal eyes, such as pig eyes, rabbit eyes, or even human eyes, are used to learn such a surgical technique for removal of the lens nucleus and the lens cortex.

In U.S. Pat. Nos. 4,865,551; 4,762,495; 4,865,552; and 4,762,496, simulation techniques have been disclosed whereby an artificial lens is disposed in a so-called "three-chamber system" to learn the aforementioned surgical technique.

Here, an artificial cornea is used with an artificial iris, which covers the artificial lens from above, and the operator opens the lens capsule through the artificial iris after opening the cornea in order to remove the artificial lens according to the prior art using common instruments. A known removal method is extraction using ultrasound (phacoemulsification).

The advantage of this separation method according to Maloney lies in that the training model can be used repeatedly under conditions which always remain the same, whereby only the artificial lens must be replaced.

However, a disadvantage of the known artificial lens is that it is only partly comparable with the human lens. According to the patents mentioned above, it comprises an alginate with the addition of plastic components, a fact which is associated with the disadvantage that lens removal cannot be realistically performed using the aforementioned phacoemulsification.

In phacoemulsification, the lens must be divided into various sections by the operator. These individual sections are then fragmented using ultrasound and aspirated. Because of the relatively unfavorable properties of the lens material used, with the Maloney lens it is possible only with difficulty to divide the lens into various sections comparable to the human operation. The sections cannot be separated; instead, they disintegrate and crumble.

The usual practice for this is to split the lens into a total of four parts. The subsequent phacoemulsification then results in the fact that the lens particles of the known Maloney lens block the aspiration system in the ultrasound hand tool used for the hose system.

According to another operation technique, the lens nucleus is removed as a whole from the capsular sac.

This second so-called extracapsular operation technique cannot be performed with the so-called Maloney system with the rigid three chamber system.

Consequently, the object of the invention is to improve a lens of the type mentioned above such that it has significantly better homogeneity and improved elasticity, and largely corresponds overall with the human lens in its mechanical properties.

SUMMARY OF THE INVENTION

To achieve this object, in accordance with the present invention there is provided an artificial lens which specifically simulates the lens of the human eye in its mechanical properties. The artificial lens comprises a purified peptide mixture. In one type of embodiment, the lens is constructed in at least two layers; in other embodiments, the lens has a homogeneous structure throughout.

BRIEF DESCRIPTION OF THE DRAWINGS

The invention may be better understood with reference to the accompanying drawings, in which.

DETAILED DESCRIPTION OF THE INVENTION

Figure 1:
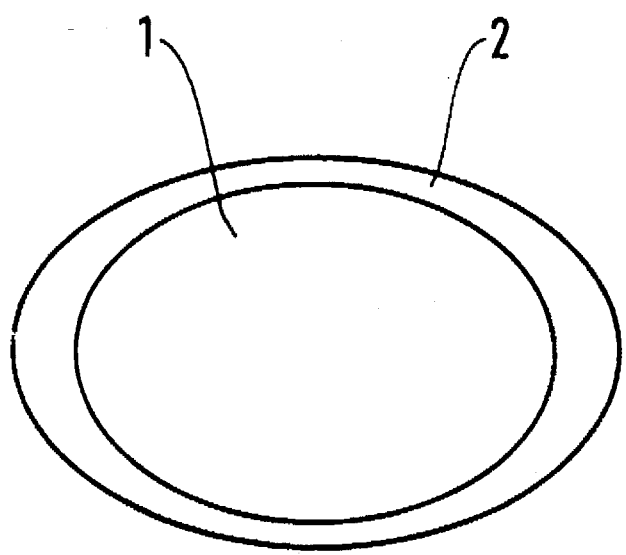
FIG. 1 is a view of a lens comprising a nucleus and a layer completely enveloping it.

An essential characteristic of the invention in a first form is that the lens according to the present invention comprises or consists preferably for the most part of a purified peptide mixture with broad molar-mass distribution (i.e., a mass of 60,000 to 90,000), whereby the purified peptide is a biologically low-grade protein because of its low content of methionine and tyrosine and the lack of cystine and tryptophan.

This lens can be structured so as to be multilayered.

In another embodiment, provision is made that the lens intrinsically has regions of differing properties, whereby a multilayered structure is preferred. Here, a hard nucleus is enveloped by preferably one or even a plurality of shells surrounding the nucleus. The shells can partially or completely envelope the nucleus, whereby complete enveloping is preferred. For this, the nucleus is first fabricated in known manner and then cast with or sprayed with the first shell. Additional shells can be applied successively as needed.

The bond between the nucleus and the shells as well as the shells with each other occurs either by means of the peptides themselves, which form bridges between the layers, or by means of appropriate binders in the form of special adhesives or other proteins.

For this, it is preferable that the nucleus be provided with only one shell, which completely envelopes it.

This multilayer lens corresponds in its structure much better than the homogeneous lens to the lens of the human eye and is consequently referred to as a "close-to-reality lens" or a "CTR lens".

With it, it is possible on the one hand to increase the hardness of the nucleus, since this is surrounded by one or a plurality of layers which provide shielding. On the other hand, a color delineation between the nucleus and the shells is possible, which corresponds to the difference in color between the cortex section and the nucleus of the natural lens also present in nature.

It is preferred to fabricate this CTR lens from a mixture of peptides. However, other suitable materials are also possible.

According to the invention, the purified peptide is obtained by partial hydrolysis of insoluble collagen contained in the bones, connective tissue, skin, tendons, and cartilages. The purified peptide can also be obtained from bovine bones and skin by an alkaline decomposition process at a high temperature. The purified peptide contains, preferably in aqueous solution, COO-groups and has a pH from 5.0 to 7.4. It is thus a thin, colorless, elastic, vitreously glossy substance, which is moisture sensitive and contains water in any concentration desired.

Consequently, the degree of hardness of the artificial lens can be ideally adjusted to the degree of hardness of a human cataract lens.

To regulate hardness, it is also possible to add various plastics to the lens or to the peptide mixture used. Here, the hardness of the artificial lens can also be adjusted by mixing various peptides. Detergents in particular, such as histological fixatives, may be added. A chemical hardening of the lens thus results.

The purified peptide according to the invention is insoluble in ethanol and ether and dissolves less than 0.5% in cold water, swells 5- to 10-fold with relatively high consistency (over 0.5%) in cold water without dissolving, and dissolves in hot water with swelling phenomena to a more or less viscous fluid, which approximately 1% purified peptide mixture congeals upon cooling (below 35°–40° C.) by partial reformation of the native conformation of the collagen into an elastic gelatin and can be reliquified at higher temperatures.

Through the use of different molecules, the peptide mixture can be optimally adjusted in its specific gravity and other physical properties.

Preferably, glass spheres with a diameter in the range from 1–50 μm are added.

This purified peptide mixture thus has the significant advantage that it ideally matches the human lens and corresponds to it in its physical properties. In a preferred embodiment of the inventive concept, dye additives are added in water-soluble form to alter the clouding of the purified peptide mixture to match it to the human cataract lens.

It is, of course, also possible with the multilayer lens structure to bestow on the lens nucleus physical properties different from those of the layers surrounding it, such as hardness or elasticity, density, or color, by addition of the aforementioned substances.

This different structure of nucleus and layers is absolutely essential in the production of a CTR lens.

Provision is made according to the invention that the artificial lens, comprising or consisting essentially of the purified peptide mixture, not be repositioned in a practice model according to the aforementioned US patents, but rather in a biological practice model, which consists essentially of an incised human or animal eye. This is thus an eye from which the lens has been extracted, which has been replaced with the artificial lens according to the invention instead of its own lens mass.

This replacement can be performed either by inserting the lens as a whole or by injecting the lens into the emptied capsular sac in the heated state, where it assumes the shape defined by the capsular sac and thus forms an artificial lens ideally simulating the human lens.

Accordingly, the shape of the lens (cross-section and shape) depends on the capsular sac into which the artificial purified peptide mixture is injected.

In another embodiment, provision is made that such lenses, consisting of a purified peptide mixture, are fabricated in extremely different sizes and shapes in a casting or an injection molding process, and then implanted as a whole to provide the practice model a specific lens.

The artificial lens can, of course, also be constructed as an artificial cornea.

It is also advantageous that the lens be enveloped in a special packaging material because of the danger of drying out. This packaging can be treated as a capsular sac for practice purposes, so that the experience necessary for operating can be obtained quickly.

In the construction of the lens as a cornea, the lens may advantageously also be used to learn ophthalmological operations. The need for special corneal material for this simulation operation is eliminated.

A further advantage is that the lens or the appropriate peptide mixture, possibly provided with additives, can be fragmented by ultrasound during phacoemulsification. This is significant in practicing phacoemulsification, where ultrasound is used with precision.

The extraction of the lens is performed, for example, by so-called "endophaco". This is a process whereby the lens capsule is opened at only one site such that it is possible to penetrate into the capsular sac with the ultrasound needle or with the aspiration cannula.

The access to the eye takes place here through the conventional path of the corneoscleral junction (limbus) or through the so-called pars plana. Variations of this surgical procedure and adaption to various other techniques are possible.

The lens according to the invention thus enables practice and experimentation with ultrasound instruments without having to resort to any special additional practice materials.

The difficulty for many operators who would like to learn so-called phacoemulsification is the control of the instrument during the operation. In pedal position 2, an ultrasound instrument aspirates and irrigates; in pedal position 3, ultrasound also acts on the tip of the handle. Since the peptide mixture (the object of the invention) can be removed only with ultrasound (in position 3), the operator learns the extremely important manipulation of the ultrasound energy in the eye in ideal fashion.

Here, surgery with a hard, difficult-to-operate cataract can be simulated either through an appropriate structure of the lens or by selective reduction of the phaco energy or the aspiration power.

The lens according to the invention is also suited to learning a conventional lens extraction, such as the intracapsular or extracapsular cataract operation.

The object of the present invention results not only from the object of the individual patent claims, but also from the combination of the individual claims among each other. All data and characteristics disclosed in the documents, including the abstract, are claimed as essential to the invention, to the extent that they are novel, individually or in combination, relative to the prior art.

In the following, the invention is explained in detail with reference to drawings depicting multiple embodiments. Additional characteristics according to the invention and advantages of the invention are disclosed in the drawings and the description thereof.

FIG. 1 depicts a CTR lens consisting of a core 1 and a lens cortex 2. In these, the lens cortex 2 is frequently referred to as "cortex"; the core 1 as "nucleus".

With this CTR lens, the differences between the nucleus and the cortex, which also occur in nature, can be implemented in the model not only by different properties, such as hardness, but also by a different coloration. Thus, a very good match and simulation are possible.

The lens according to the invention provides improved homogeneity and elasticity and largely corresponds in its properties to the lens of the human eye.

What is claimed is:

1. An artificial lens comprising at least two layers, the first layer defining a lens core, the second layer defining a lens cortex, said two layers being comprised of purified peptide mixtures.

2. An artificial lens according to claim 1, wherein the lens has regions with differing properties.

3. An artificial lens according to claim 1, wherein the lens core is harder than the lens cortex.

4. An artificial lens according to claim 1, wherein the peptide mixtures in aqueous solution contains primarily COO-groups with a broad molar-mass distribution from 60,000 to 90,000.

5. An artificial lens according to claim 1, wherein the peptide mixtures have a pH of 5.0 to 7.4.

6. An artificial lens according to claim 1, wherein the degree of hardness of the artificial lens is varied through the addition of additional peptides.

7. An artificial lens according to claim 1, wherein the peptide mixtures are modified by changing the molecule in its specific weight and, thus, its physical properties.

8. An artificial lens according to claim 1, wherein the peptide mixtures are adjusted in its hardness by the admixing of plastics.

9. An artificial lens according to claim 1, wherein the peptide mixtures are adjusted in its hardness by the admixing of detergents.

10. An artificial lens according to claim 1, wherein the lens is implanted, preshaped as a lens nucleus, in the eye.

11. An artificial lens according to claim 1, wherein the peptide mixtures are injected in the fluid state after heating into the eye.

12. An artificial lens according to claim 1, wherein a clouding or coloration of the lens is obtained by the addition of dyes.

13. An artificial lens according to claim 1, designed as an artificial cornea.

14. An artificial lens according to claim 1, wherein the artificial lens is injectable into an artificial eye simulation model.

15. An artificial lens according to claim 1, wherein the degree of hardness of the artificial lens is varied through the addition of additional plastics.

16. An artificial lens according to claim 1, wherein the degree of hardness of the artificial lens is varied through the addition of additional chemical detergents.

17. An artificial lens according to claim 1, wherein the degree of hardness of the artificial lens is varied through the addition of additional water.

18. An artificial lens according to claim 1, wherein the peptide mixtures are adjusted in their hardness by the admixing of histological fixative.

19. An artificial eye simulation model comprising an artificial lens according to claim 1.

20. An artificial eye simulation model according to claim 19, where the artificial lens may be used as an artificial cornea for learning ophthalmological operations.

21. An artificial eye simulation model according to claim 19, where the artificial lens may be used for learning phacoemulsification for disintegration with an ultrasonic needle.

22. An artificial eye simulation model according to claim 19, where the artificial lens may be used for learning conventional lens extraction such as intracapsular or extracapsular cataract surgery.

* * * * *